US008685038B2

(12) United States Patent
Imran

(10) Patent No.: US 8,685,038 B2
(45) Date of Patent: Apr. 1, 2014

(54) IONTOPHORETIC APPARATUS AND METHOD FOR MARKING OF THE SKIN

(75) Inventor: Mir Imran, Los Altos Hills, CA (US)

(73) Assignee: Incube Labs, LLC, San Jose, CA (US)

( * ) Notice: Subject to any disclaimer, the term of this patent is extended or adjusted under 35 U.S.C. 154(b) by 129 days.

(21) Appl. No.: 12/632,647

(22) Filed: Dec. 7, 2009

(65) Prior Publication Data
US 2011/0137307 A1    Jun. 9, 2011

(51) Int. Cl.
*A61B 17/00*    (2006.01)
(52) U.S. Cl.
USPC ........................................ 606/116
(58) Field of Classification Search
USPC ............... 606/41, 116, 185, 186, 189, 167; 604/19–22, 289, 290, 890.1, 501, 604/892.1; 607/1, 901, 2, 9, 75, 152, 153; 600/372, 395; 424/63; 81/9.22; 433/88, 433/86, 89, 32; 204/450, 600
See application file for complete search history.

(56) References Cited

U.S. PATENT DOCUMENTS

| | | |
|---|---|---|
| 3,491,187 A | 1/1970 | Ely |
| 5,555,899 A | 9/1996 | Foreman |
| 5,693,024 A | 12/1997 | Flower |
| 5,911,223 A * | 6/1999 | Weaver et al. ............. 128/898 |
| 5,983,130 A | 11/1999 | Phipps et al. |
| 6,330,471 B1 | 12/2001 | Higo et al. |
| 6,512,950 B2 | 1/2003 | Li et al. |
| 6,553,255 B1 | 4/2003 | Miller et al. |
| 6,689,275 B1 | 2/2004 | Gupta |
| 6,743,015 B2 * | 6/2004 | Magnani ........................ 433/80 |
| 6,779,468 B1 | 8/2004 | Gupta |
| 6,800,122 B2 | 10/2004 | Anderson et al. |
| 7,137,975 B2 | 11/2006 | Miller et al. |
| 7,340,297 B2 | 3/2008 | Tamarkin et al. |
| 7,390,384 B2 | 6/2008 | Fang et al. |
| 7,437,189 B2 | 10/2008 | Matsumura et al. |
| 7,496,401 B2 | 2/2009 | Bernabei |

(Continued)

FOREIGN PATENT DOCUMENTS

| | | |
|---|---|---|
| EP | 1374944 A1 | 1/2004 |
| JP | 2000-342697 A | 12/2000 |
| KR | 2009-0009330 U | 9/2009 |

OTHER PUBLICATIONS

International Search Report and Written Opinion mailed Aug. 31, 2011 in International App. PCT/US2010/059323.

(Continued)

*Primary Examiner* — Thomas McEvoy
*Assistant Examiner* — Jocelin Tanner
(74) *Attorney, Agent, or Firm* — Mahamedi Paradice Kreisman LLP

(57) ABSTRACT

Embodiments provide apparatus and methods for producing markings in the skin. One embodiment provides an apparatus for marking the skin comprising a housing and reservoir for storing a skin colorant. An electrode is positioned within the housing so as to be electrically coupled to the colorant in the reservoir and is configured to be coupled to a current source and return electrode. A colorant applicator having at least one fluid pathway is coupled to a housing distal end. The applicator proximal end is positioned such that the fluid pathway is coupled with the reservoir. The applicator distal end applies colorant to the skin surface through the fluid pathway as the applicator is moved across the skin. The electrode delivers current from the current source to the skin to transport charged pigment elements of the colorant into the skin using an electromotive driving force to produce a marking in the skin.

18 Claims, 7 Drawing Sheets

(56) References Cited

U.S. PATENT DOCUMENTS

| | | |
|---|---|---|
| 7,522,954 B2 | 4/2009 | Tedoldi |
| 7,548,778 B2 | 6/2009 | Roy |
| 7,558,625 B2 | 7/2009 | Levin et al. |
| 7,590,444 B2 | 9/2009 | Tanioka |
| 7,593,770 B2 | 9/2009 | Lerner |
| 7,611,481 B2 | 11/2009 | Cleary et al. |
| 7,651,475 B2 | 1/2010 | Angel et al. |
| 7,660,626 B2 | 2/2010 | Tanioka et al. |
| 2004/0138646 A1 | 7/2004 | Walla |
| 2004/0267283 A1* | 12/2004 | Mavor et al. ............ 606/116 |
| 2005/0020487 A1 | 1/2005 | Klaus et al. |
| 2005/0165393 A1 | 7/2005 | Eppstein |
| 2005/0209565 A1 | 9/2005 | Yuzhakov |
| 2005/0267399 A1* | 12/2005 | Tedoldi ................... 604/20 |
| 2006/0216339 A1 | 9/2006 | Ambron et al. |
| 2006/0229549 A1 | 10/2006 | Hause et al. |
| 2006/0258973 A1 | 11/2006 | Volt |
| 2007/0065521 A1 | 3/2007 | Venkataraman et al. |
| 2007/0066934 A1 | 3/2007 | Etheredge et al. |
| 2007/0083185 A1 | 4/2007 | Carter |
| 2008/0058699 A1 | 3/2008 | Hause et al. |
| 2008/0058700 A1 | 3/2008 | Hause et al. |
| 2008/0081051 A1 | 4/2008 | Sabin et al. |
| 2008/0213855 A1* | 9/2008 | Firth et al. ............ 435/173.6 |
| 2008/0287497 A1 | 11/2008 | Anderson et al. |
| 2009/0036821 A1 | 2/2009 | Lai |
| 2009/0062720 A1 | 3/2009 | Anderson et al. |
| 2009/0163597 A1 | 6/2009 | Goto et al. |
| 2009/0171313 A1 | 7/2009 | Yamamoto et al. |
| 2009/0221985 A1 | 9/2009 | Bukshpan et al. |
| 2009/0254018 A1 | 10/2009 | Nakayama et al. |
| 2009/0259176 A1 | 10/2009 | Yairi |
| 2009/0281475 A1 | 11/2009 | Nisato et al. |
| 2009/0299264 A1 | 12/2009 | Matsumura et al. |
| 2009/0299267 A1 | 12/2009 | Durand |
| 2010/0010418 A1 | 1/2010 | Nisato |
| 2010/0191171 A1* | 7/2010 | Park ....................... 604/20 |

OTHER PUBLICATIONS

International Preliminary Report on Patentability as issued in corresponding International application PCT/US2010/059323, dated Jun. 21, 2012.

* cited by examiner

IONTOPHORETIC APPARATUS AND METHOD FOR MARKING OF THE SKIN

FIELD OF THE INVENTION

Embodiments described herein relate to intradermal delivery of colorants for producing skin markings. More specifically, embodiments described herein relate to intradermal iontophoretic delivery of colorants for producing skin markings.

BACKGROUND

The skin consist of three main layers: the epidermis (the outermost layer), the dermis and subcutaneous tissue. Tattooing or marking of the skin involves embedding dyes into one or both of the epidermal or dermal layers. Typically, this is done using needles. However, use of needles is a painful process which has various associated health risks including infection (e.g., from contaminated needles) allergic and phototoxic reactions. Also, many of the dyes currently used can fade over time. Thus, there is need in the art for improved tattooing methods of the skin.

BRIEF SUMMARY

Embodiments described herein provide methods for using electrically based intradermal delivery methods such as intradermal iontophoresis for producing markings or tattoos in the skin.

One embodiment of the invention provides an apparatus for producing markings in the skin comprising a housing having a proximal and distal end and a reservoir for the storage of a skin colorant. A portion of the housing is configured to be held in the hand of a user. An electrode is positioned within the housing with a portion positioned to be electrically coupled to the skin colorant in the reservoir. The electrode is configured to be electrically coupled to a current source and a return electrode. A colorant applicator is coupled to the distal end of the housing. The applicator has a proximal and distal end and at least one fluid pathway. The proximal end of the applicator is positioned such that the at least one fluid pathway is coupled with the reservoir. The distal end of the applicator is configured to apply colorant to the skin surface through the at least one fluid pathway as the applicator is moved across the skin. The electrode is configured to deliver current from the current source to the skin to transport charged pigment elements of the colorant into the skin using an electromotive driving force to produce a marking in the skin from the pigment elements.

The at least one fluid pathway can comprise a lumen extending from the proximal to the distal end of the applicator or a portion thereof with fluid be delivered through the pathway. The size and material properties of the lumen can be configured to deliver the fluid using capillary action and in particular embodiments, the walls of the lumen can be treated to enhance the driving forces of capillary action. In preferred embodiments, the applicator can comprise a felt or other porous material such that the applicator wicks colorant from the reservoir onto the skin as the applicator tip is passed over the skin. In such embodiments, the at least one fluid path way comprises a plurality of pathways. Use of felt or other porous material for the applicator also allows the tip of the applicators to act as a dispersion element to disperse or distribute current at the interface between the applicator and the skin surface by providing a plurality of conductive pathways to the skin surface. Additionally, it allows for the applicator to be conformable to the contour of the skin surface as the applicator is moved across the skin. Other conformable materials may also be used.

In various embodiments, the distal end or other portion of the applicator can be shaped or otherwise configured to produce a selectable current density at the interface between the applicator and the skin surface. In particular embodiments, such as those employing felt, foam or another porous material, the distal portion of the applicator can be configured as a current dispersion element which disperses or distributes current at the interface between the applicator and the skin surface by providing a plurality of conductive pathways to the skin surface. In other embodiments, the applicator can include a current concentrating element such as a hollow stylus or tube that allows for the concentration of current density at the interface between the applicator and the skin surface. The current concentrating element can be attached to the porous applicator tip so that current is more concentrated (yielding a higher current density) in one location and less concentrated (yielding a lower current density), in another location. This gradient in current densities can be used to drive varying amounts of colorant into the skin over a selected target site to produce darker and lighter areas of markings and/or drive the colorant to varying depths in the skin to produce a similar effect.

The electrode can comprise various materials including stainless steel, other conductive metals as well as carbon, for example, graphite. All or a portion of the electrode can be positioned in the reservoir and electrode is desirably positioned to minimize a voltage drop between the distal tip of the electrode and the colorant applied to the skin. In particular embodiments, the electrode can include a dielectric coating such that there is no flow of electrons between the electrode and the skin surface. Instead, current flows by means of capacitive coupling of the electrode to the colorant and the skin surface. Such embodiments minimize electrochemical degradation of the electrode and prevent unwanted migration of electrode materials into the skin.

The apparatus can include a controller such as a microprocessor for controlling one or more operational aspects of the apparatus including iontophoretic current and voltage and waveforms, and colorant delivery including rates and amounts. In many embodiments, the apparatus can also include an integral power source such as a lithium ion or other portable battery. In such embodiments, the apparatus can include various power conditioning circuits such as DC-AC converters to provide both alternating and direct current. In other embodiments, the apparatus can be coupled to an external current source such as an AC or DC source by means of one or more electrical connectors.

The reservoir can be sized to allow for varying time periods of operation depending upon the colorant delivery rate. In various embodiments, the housing can include an optically transparent window to allow a user to ascertain the level of colorant in the reservoir. Also the reservoir may contain a sensor for determining an amount of colorant in the reservoir as well as other parameters such as conductivity/impedance of the colorant. In particular embodiments, the reservoir can include multiple compartments to allow for delivery of different colorants or combinations of colorants. Each compartment can be coupled to the applicator by means of a control valve or like device to allow a user to switch and combine colorants during the application process.

In an exemplary embodiment of a method of using the invention to mark the skin, the apparatus is coupled to a power source and a return electrode which is positioned on the skin near the target site for marking. The user then places the applicator tip on the target site for marking and may keep the tip stationary or may move the tip across the surface of the skin. Colorant is delivered from the tip to the skin surface using the felt or other porous tip of the applicator. Current is then delivered from the electrode to ionize the colorant and transport the colorant a selected depth into the skin using an electromotive force from the voltage associated with the current. The colorant then produces a marking at the delivered location in the skin from the pigment. Typically, the driving force is an iontophoretic driving force whereby the charged ionized compounds in the colorant are repelled by a like charge from the electrode and migrate into the skin as a result. The colorant can comprise an ionizable pigment such as various iron containing compounds. The colorant may also comprise chargeable nano-particles such as hematite particles which contain a pigment compound. The current can include alternating or direct current as well as combinations thereof. In specific embodiments, the delivered current can comprise a DC component and an AC component. The AC component can be configured to discharge and thus breakdown the build-up of capacitive charge in skin tissue which may impede the migration of colorant into the skin. Also in various embodiments, the current can be modulated (e.g., by changing the waveform, frequency, amplitude, etc) to control the penetration depth of colorant into the skin as well as reduce the pain perception of a person receiving a marking.

The markings produced by the apparatus can be used for decorative, medical and identification purposes. For the latter two applications, magnetic colorants such as those containing ferrite materials can be used such that they can be detected and read trans-dermally by a magnetic reading device such as a hand held magnetic reader. In use, such embodiments allow a medical practitioner to pre-operatively mark a limb or other portion of the body to be operated on with magnetically readable marking indicating that is the limb or body portion to be operated on. Then immediately prior to surgery, the surgeon would scan the limb with the magnetic reading device to ensure that the limb is the correct limb. Theses and related embodiments serve to reduce the likelihood of error of the wrong limb or other body part being operated on. In related embodiments, the contra-lateral limb which is not be to be operated on can be intradermally marked with readable indicia indicating that it is not the limb to be operated on. In use, such embodiments provide two levels of quality assurance to ensure the correct limb or other intended portion of the anatomy is operated on. That is, before a limb can be operated on, the surgeon must verify to make sure that it is the correct limb and also that it is not the incorrect limb. Such embodiments are particularly useful for reducing the likelihood of human error during a surgical or other medical procedure in operating on the wrong limb or other portion of the anatomy.

Further details of these and other embodiments and aspects of the invention are described more fully below, with reference to the attached drawing figures.

DETAILED DESCRIPTION OF THE INVENTION

Figure 1:
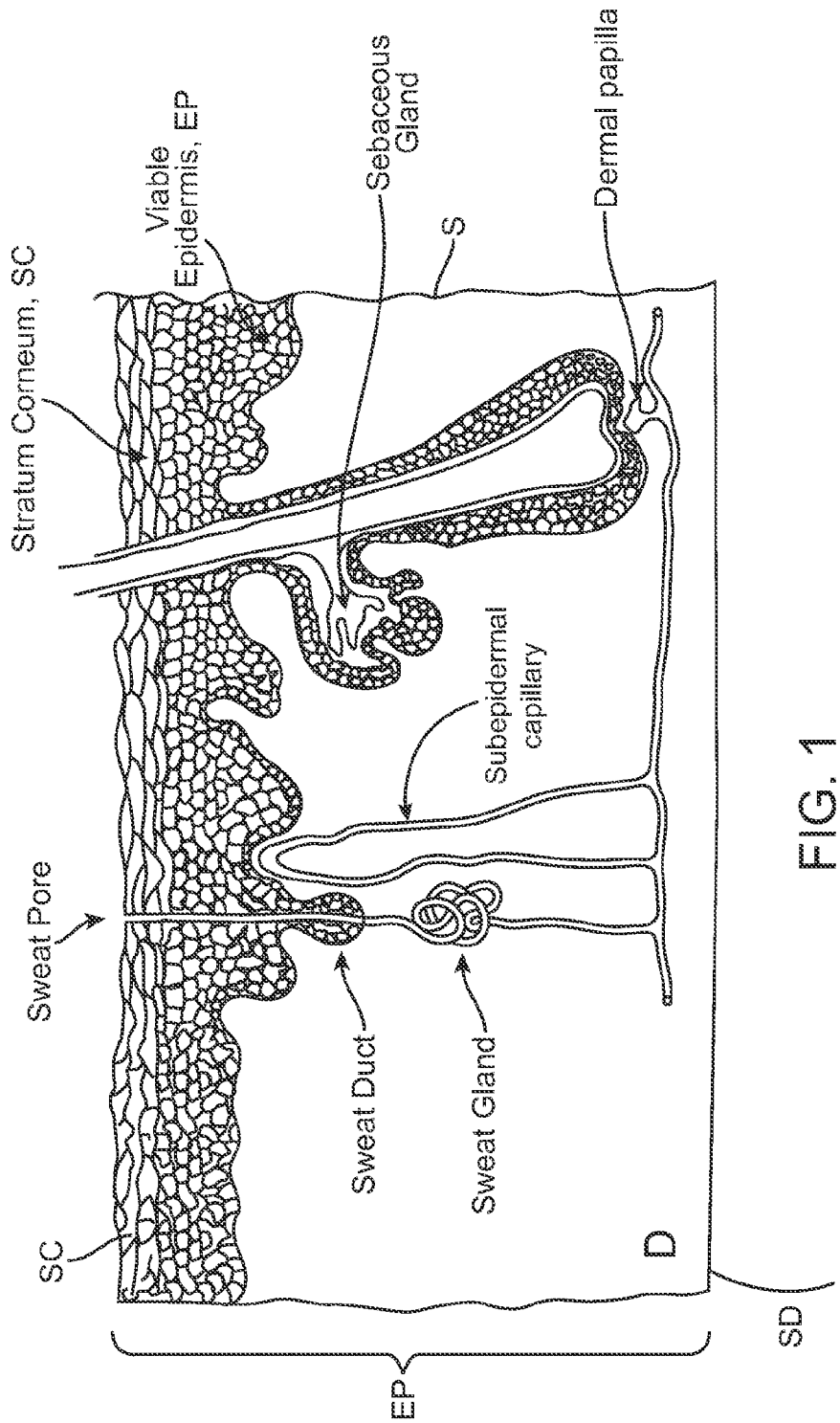
FIG. 1 is a cross sectional view showing the three main layers of the skin, the epidermis, the dermis and subcutaneous tissue.

Many embodiments described herein provide a system and method for intradermal iontophoretic delivery of colorants to produce markings in the skin. A brief explanation will be provided for these terms as well as the anatomy of the skin. Referring now to FIG. 1, the layers of the skin include the epidermis EP, dermis D and subdermis SD. The upper most layer of the epidermis includes the stratum corneum SC a dead layer of skin (having a thickness of about 10 to 40 µm) and the viable epidermis EP. The term intradermal refers to the delivery of a substance such as a colorant into the skin S including one or both of the epidermal E and dermal D layers.

Iontophoresis is a non-invasive method of propelling high concentrations of a charged substance, known as the active agent, into or through the skin by repulsive electromotive force using a small electrical charge. The charge is applied by an electrical power source to an active electrode assembly placed on the skin which contains a similarly charged active agent and a solvent in which it is dissolved. Current flows from the electrode assembly through the skin and then returns by means of a return or counter electrode assembly also placed on the skin. A positively charged electrode assembly, termed the anode will repel a positively charged active agent, or anion, into the skin, while a negatively charged electrode assembly, termed the cathode, will repel a negatively charged active agent, known as a cation into the skin.

As used herein, a colorant is a substance (solid or liquid) that imparts a color change to the skin by changing the color of light the colorant reflects as a result of selective color absorption by the colorant. Colorants may include both dyes and pigments. A pigment will typically exist in solid form though it can be suspended in a liquid. A dye can be dissolved in liquid and can chemically bind to a substrate substance such as collagen and other molecular components of the skin. A pigment imparts color to the skin by being deposited within the layers of the skin.

Referring now to FIGS. 2-7, an embodiment of a system for the intradermal iontophoretic delivery of a colorant 200 to a tissue site TS on or into the skin S of patient, comprises an iontophoretic apparatus 10, coupled to a return electrode 20 and a power source 100. Apparatus 10 (also referred to herein as handpiece 10) comprises a housing 30, a colorant applicator 40 (herein applicator 40), an electrode 50 and a reservoir 60. Housing 30 includes proximal and distal ends 31 and 32 (distal being the end coming into contact with skin) a handle portion 33 configured to be held in the hands of a user. Power source 100 can be an external source 100e such as an AC or DC power supply or an integral power source 100i such as a portable battery, for example, an alkaline, lithium ion or other portable battery known in the art. Apparatus 10 will also typically include a controller 90, such as a microprocessor or other logic resources known in the art, for controlling one or more aspects of the marking process including iontophoretic current and voltage levels and waveforms and colorant selection and delivery (e.g., rates and amounts).

Applicator 40 has proximal and distal ends 41 and 42 and includes at least one fluid pathway 43 for delivering colorant 200 to skin S. The proximal applicator end 41 is coupled to housing distal end 32 and is positioned such that the at least one fluid pathway 43 is coupled to reservoir 60 so that colorant 200 can flow through the fluid pathway to the skin. Applicator 40 can comprise a solid material such as various plastics or in preferred embodiments, a porous material such as polymer foam or fibrous matting fabricated from various polymer fibers. Suitable fibers including various cottons, PETS and various felt materials known in the art. The distal applicator end 42 is configured to move along the skin surface and deliver colorant 200 to the skin through fluid pathway 43. The distal end 42 can be shaped or otherwise configured to allow for a selectable width of colorant to be applied to the skin. In particular embodiments, the distal end 42 can have pointed or angled shape similar to those found on magic markers. In these and related embodiments, the applicator can comprise a felt tip having the desired shape.

Figure 3:
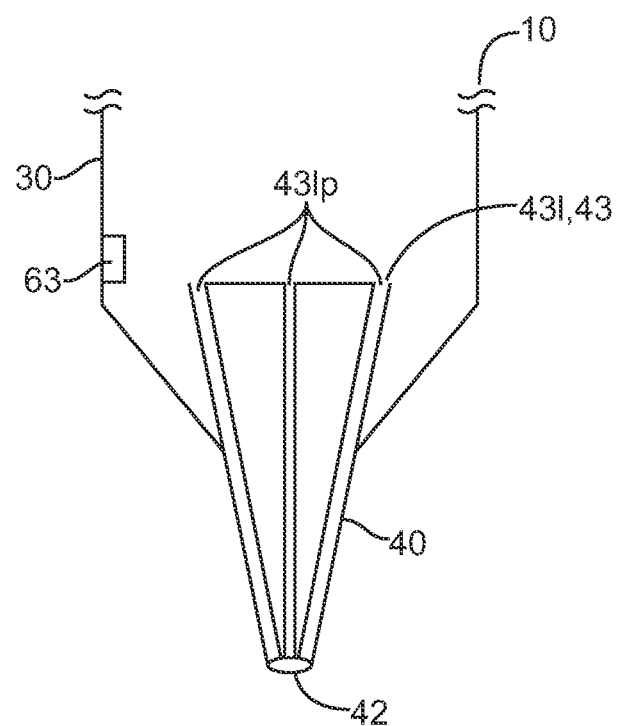
FIG. 3 shows an embodiment of a colorant applicator having a plurality of lumens.
Figure 4:
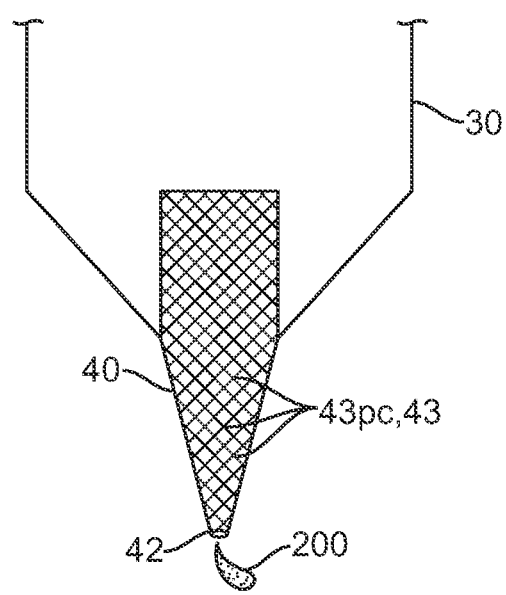
FIG. 4 shows an embodiment of a porous colorant applicator.
Figure 5:
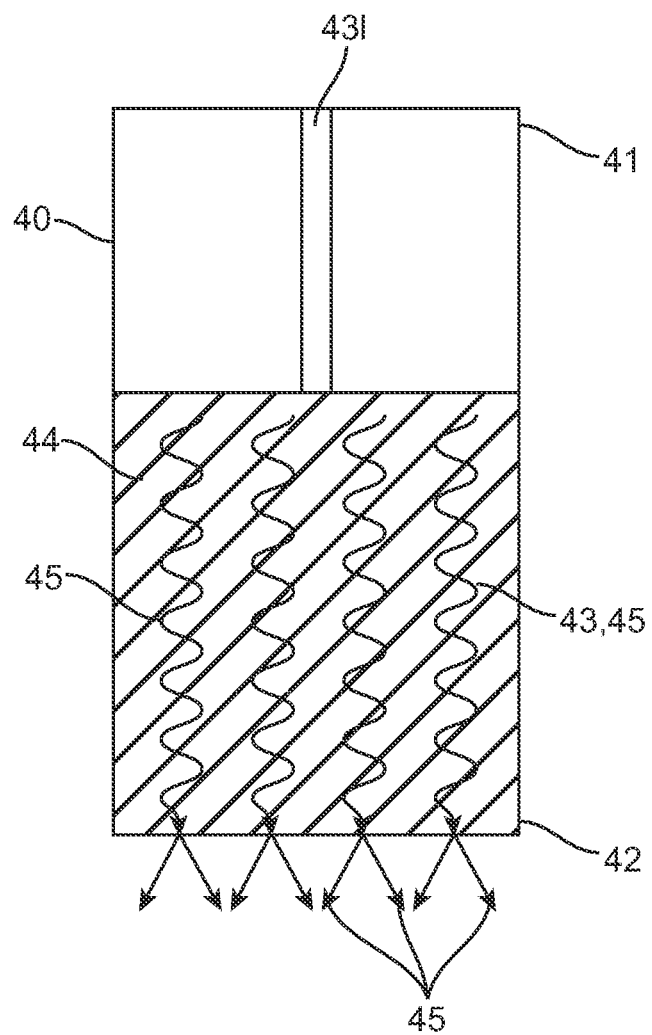
FIG. 5 shows an embodiment of a porous applicator.
Figure 6:
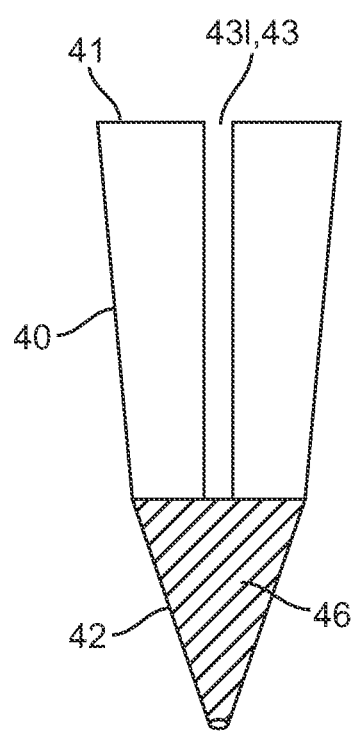
FIG. 6 shows an embodiment of an applicator having a current concentrating element.

The fluid pathway 43 will typically comprise a lumen $43l$ extending through all or a portion of the applicator 40. It may also comprise a plurality $43lp$ of lumens $43l$ as shown in the embodiment of FIG. 3. The size and material properties of lumens $43l$ can be configured to deliver the fluid using capillary action and in particular embodiments, the walls of the lumen can be treated to enhance the driving forces of capillary action. For embodiments having a porous applicator 40, the fluid pathways 43 can comprise a plurality of porous channels $43pc$ within the porous structure of applicator 40 as is shown in the embodiment of FIG. 4. In these and related embodiments, the porosity and surface tension of the applicator 40 can be selected to control the amount of colorant delivered through the applicator to the skin. For example, more porous materials can be selected to deliver greater amounts of colorant to the skin.

In various embodiments, the distal portion 48 or other portion of the applicator 40 can be shaped or otherwise configured to produce a selectable current density at the interface between the applicator and the skin surface. In particular embodiments, such as those employing felt, foam or another porous material for applicator 40, the distal portion 48 can be configured as a current dispersion element 44 which disperses or distributes current at the interface between the applicator and the skin surface by providing a plurality of conductive pathways 45 to the skin surface though fluid pathways 43. In use, the current dispersion element 44 reduces the likelihood of heating or thermal injury to the skin during the marking process, by providing a plurality of alternative pathways for current to flow into the skin should the impedance at any one single pathway become too great.

In alternative embodiments, the applicator 40 can include a current concentrating element 46 such as a hollow stylus or tube that allows for the concentration of current density at the interface between the applicator and the skin surface. The current concentrating element 46 can be attached to applicator distal end 42 so that current is more concentrated (yielding a higher current density) in one location and less concentrated (yielding a lower current density), in another location. This gradient in current densities can be used to drive varying amounts of colorant 200 into the skin over a selected target site to produce darker and lighter areas of markings and/or drive the colorant to varying depths in the skin to produce a similar effect.

The housing 30 can have a pen like or other elongated shape and can be fabricated from various rigid polymers known in the art, e.g., polystyrene, polycarbonate, PET. Etc which can be configured to be sterilized using EtO, steam, radiation or other sterilization method known in the art. Handle portion 33 can be positioned near proximal end 31 and can have a finger grip configuration have a knurled or other friction surface, allowing the user to hold the handle in much the same way he or she would hold a pen. In particular embodiments, handle portion 33 can comprise a section having a wider diameter than the remainder of housing 30. Handle portion 33 can also include an insulating layer to prevent or reduce the likelihood of any current flowing into the operator.

Housing 30 can also include one or more electrical/data connectors 34 such as various lemo-connectors for coupling to power source 100 as well as a USB connector for coupling to an external electronic device such as a computer, PDA, and the like. RF and infrared ports are also contemplated for communicating with an external device such as a cell phone. It may also include various fluidic connectors 35, (e.g., luer-lock connectors) for coupling to pressure/vacuum sources and external reservoirs of colorant or other liquid source (e.g., saline, or other aqueous solution).

Housing 30 also includes at least one reservoir 60 for storage of colorant 200 which is delivered to skin S. Reservoir 60 can be configured to hold selectable volumes of colorant, for example, in the range from 5 to 100 ml, with specific embodiments of 10, 20, and 50 ml. As is described below, applicator 40 is fluidically coupled to the reservoir 60 to allow colorant to be delivered from the reservoir to the skin surface. Also is described below, in many embodiments, at least a portion of electrode 50 can be positioned within the reservoir to allow the electrode to be conductively coupled to the colorant 200 in the reservoir so as to conduct current to the colorant in the reservoir.

Figure 7:
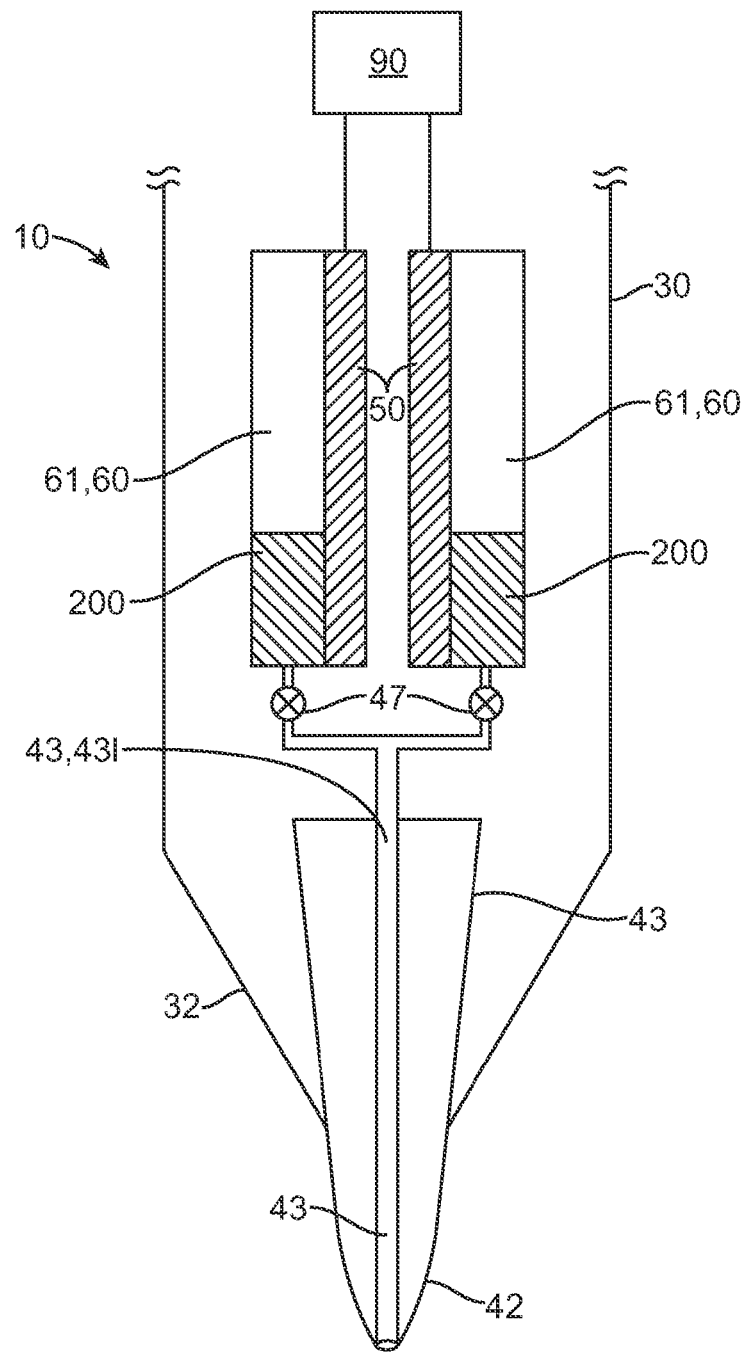
FIG. 7 shows an embodiment of a handpiece for marking the skin having multiple colorant reservoirs.

In various embodiments, reservoir 60 can include multiple compartments 61 to allow for delivery of different colorants and/or combinations of colorants as is shown in the embodiment of FIG. 7. Each compartment 61 can be coupled to the applicator 40 by means of a control valve 47 or like device to allow a user to switch and combine colorants 200 during the application process. Such switching can allow the operator to select a particular colorant 200 or combine them to produce a different color. Additionally, colorants having different conductive properties can also be selected through such an approach. For example, colorants that are more readily ionizable and/or have a greater charge can be selected by the operator manually when they wish to have greater penetration of the colorant. Colorant selection can also be done under control of a controller 90 in response to one or more sensed inputs on the conductive properties of the skin, e.g., skin conductivity, impedance, capacitance, etc. In this way, when the conductive properties of the skin change (e.g., decrease due to increased impedance), rather than necessarily switching to a higher power setting, the controller can switch to use of a colorant which is more conductive and thus reduces the power requirements to achieve the desired amount and depth of colorant penetration. The switching between compartments and colorants can be controlled by a controller 90 such as processor; and/or it may also be done manually under operator control.

Figure 2:
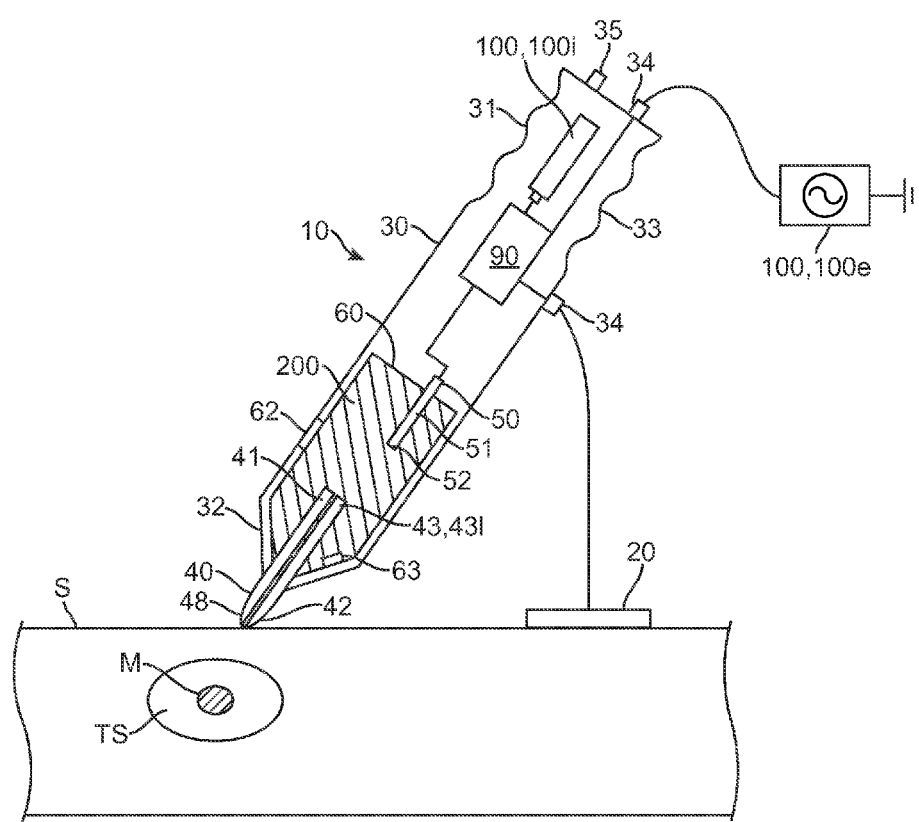
FIG. 2 is a schematic view of an embodiment of a system for marking the skin including a handpiece and return electrode.

In particular embodiments, reservoir 60 can include a window 62 which is integral with housing 30 to allow an operator to ascertain how much colorant is left in the reservoir as is shown in the embodiment of FIG. 2. The reservoir may also include a sensor 63 for determining the volume of colorant left in the reservoir and/or when the reservoir is empty as is shown in the embodiments of FIG. 2 and FIG. 3. Sensor 63 can any volumetric sensor known in the art and can include various impedance-based sensors. Sensor 63 can also be used to determine the impedance of colorant 200 and signal this value to a controller 90 or power regulation circuitry so as to regulate the current and voltage and waveforms supplied to electrode 50.

Electrode 50 can comprise various conductive materials including stainless steel, other conductive metals as well as various graphite materials and carbon impregnated materials. Suitable graphites include flexible compressed graphite and pyrolytic graphite. In alternative embodiments, the electrode can comprise a carbon impregnated polymer such as rubber or even polymer fibers such as cotton, polyesters, polysulphone other polymeric fibers known in the art.

A variety of arrangements and configuration are contemplated for electrode 50. In preferred embodiments, a portion 51 of the electrode 50 is positioned in the reservoir 60 so as to conductively couple the electrode to colorant 200, though as an alternative, the electrode can be conductively coupled to the reservoir through a wire or other conductive means. Desirably, electrode 50 is positioned to minimize a voltage drop between the distal tip 52 of the electrode and the colorant applied to the skin. In particular embodiments, the distal tip 52 of the electrode 50 can include a dielectric coating such that there is no flow of electrons between the electrode and the skin surface. Instead, current flows by means of capacitive coupling of the electrode to the colorant and the skin surface. Such embodiments minimize electrochemical degradation of the electrode and prevent unwanted migration of electrode materials into the skin.

The colorant 200 can comprise a variety of ionizable pigments. Suitable colorants 200 can include various iron containing compounds. The colorant may also comprise chargeable particles including nano-particles which contain a pigment compound. Suitable nano-particles include hematite and other related particles. Suitable pigment compounds include various azo compounds and related derivatives including red and blue based compounds. Azo compounds comprise compounds bearing the functional group R—N=N—R', in which R and R' can be either an aryl or alkyl. In still other embodiments, colorant 200 can comprise various chemical and biochemical compounds which are configured to produce or change color upon the occurrence of a particular biochemical or physiologic reaction, for example, an allergic reaction, or infection. In related embodiments the colorants can be configured to change color to detect qualitative or quantitative changes in a bioanalyte, for example, blood glucose, for the detection of a physiological condition such as hyperglycemia. In other embodiments, the colorant can be configured to detect pregnancy, or the onset of ovulation.

The charge to mass ratio of the particle and pigment compound can be selected to achieve a selectable level of penetration of the particle into the skin for a given iontophoretic driving force/voltage. Determination of the charge to mass ratio can be determined theoretically and/or empirically by using standard transdermal methods known in the art including performance of in vitro experiments using pig or other skin as a model.

In an exemplary embodiment of a method using the invention to mark the skin, apparatus 10 is coupled to a power source 100 and a return electrode 20 which is positioned on the skin S near a target site TS for marking. The user then places the applicator tip 42 on the target site TS for marking and may keep the tip stationary or may move the tip across the surface of the skin. Colorant 200 is delivered from the tip 42 to the skin surface using the felt or other porous tip of the applicator. Current is then delivered from the electrode to ionize the colorant and transport the colorant a selected depth into the skin using an electromotive force from the voltage associated with the current. The colorant then produces a marking M at the delivered location in the skin from the colorant. The current can include alternating or direct current as well as combinations thereof. In specific embodiments, the delivered current can comprise a DC component and an AC component. The AC component can be configured to discharge and thus breakdown the build-up of capacitive charge in skin tissue which may impede the migration of colorant into the skin. Also in various embodiments, the current can be modulated (e.g., by changing the waveform, frequency, amplitude, etc.) to control the penetration depth of colorant into the skin as well as reduce the pain perception of a person receiving a marking. The particular amount of current modulation can be tuned or fine tuned for a specific patient prior to the making of a marking. In one example, tuning can involving varying the frequency of the AC signal, while soliciting feedback from the patient on their pain level.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, the iontophoretic patch can be modified in size, shape and dose of therapeutic agent for different medical conditions, different tissue sites as well as for various pediatric applications.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. An apparatus for producing markings in the skin, the apparatus comprising:
    a housing having a proximal and distal end and a reservoir for the storage of a skin colorant, a portion of the housing configured to be held in the hand of a user;
    a colorant applicator coupled to the distal end of the housing, the applicator having a proximal and distal end and at least one fluid pathway, the proximal end positioned within the reservoir such that the at least one fluid pathway is coupled with the reservoir, the distal end configured to apply colorant to the skin surface through the at least one fluid pathway as the applicator is moved across the skin; and
    an electrode positioned within the housing, a portion of the electrode extending into the reservoir and terminating proximal to the proximal end of the applicator to allow that portion of the electrode to be immersed in and electrically coupled to the skin colorant in the reservoir, another portion of the electrode extending out of the reservoir and, configured to be electrically coupled to a current source and a return electrode;
    wherein the electrode is configured to deliver current to the skin to transport charged pigment elements of the colorant into the skin using an electromotive driving force to produce a marking in the skin from the pigment elements.

2. The apparatus of claim 1, wherein at least a portion of the applicator comprises a porous material which includes a plurality of fluid pathways.

3. The apparatus of claim 1, wherein the at least one fluid pathway comprises a lumen.

4. The apparatus of claim 3, wherein the lumen extends from the proximal to the distal end of the applicator.

5. The apparatus of claim 4, wherein a surface of the lumen is treated to enhance capillary action of the colorant through the at least one lumen.

6. The apparatus of claim 1, wherein the distal end of the applicator is conformable to the contours of the skin as the applicator is moved across the skin.

7. The apparatus of claim 1, wherein the applicator includes a current concentrating element configured to concentrate current density at an interface between the applicator and the skin surface.

8. The apparatus of claim 1, wherein the applicator includes a current dispersing element configured to disperse current density at an interface between the applicator and the skin surface.

9. The apparatus of claim 1, wherein a distal tip of the electrode is positioned within a selected distance of the applicator distal end so that a voltage drop between the distal tip of the electrode and the applicator distal tip is negligible.

10. The apparatus of claim 1, wherein the electrode comprises metal, stainless steel or carbon.

11. The apparatus of claim 1, wherein a surface of the electrode includes a dielectric coating configured to capacitively couple the electrode to the colorant such that there is no direct flow of electrons between the electrode and the skin surface.

12. The apparatus of claim 1, wherein the applicator distal end is shaped to produce a selectable current density.

13. The apparatus of claim 1, wherein the current source is a battery.

14. The apparatus of claim 1, wherein the return electrode is coupled to the current source, the return electrode configured to be placed on the skin.

15. The apparatus of claim 1, wherein the portion of the electrode positioned within the reservoir is longer than the portion extending out of the reservoir.

16. The apparatus of claim 1, further comprising a volumetric sensor disposed within the reservoir, the volumetric sensor being configured to determine a volume of skin colorant left in the reservoir.

17. The apparatus of claim 1, further comprising an impedance sensor configured to determine an impedance of the skin colorant.

18. An apparatus for producing markings in the skin, the apparatus comprising:
   a housing having a proximal and distal end and a reservoir for the storage of a skin colorant, a portion of the housing configured to be held in the hand of a user;
   an electrode positioned within the housing having a distal portion and a proximal portion, the distal portion of the electrode being immersed in and electrically coupled to the skin colorant in the reservoir, the proximal portion of the electrode extending proximal to the reservoir to be electrically coupled to a current source, via a conductive line, and a return electrode; and
   a colorant applicator coupled to the distal end of the housing, the applicator having a proximal and distal end and at least one fluid pathway, the proximal end positioned within the reservoir such that the at least one fluid pathway is coupled with the reservoir, the distal end configured to apply colorant to the skin surface through the at least one fluid pathway as the applicator is moved across the skin; and
   wherein the electrode is configured to deliver current to the skin to transport charged pigment elements of the colorant into the skin using an electromotive driving force to produce a marking in the skin from the pigment elements.

* * * * *